US009290452B2

(12) United States Patent
Hafner et al.

(10) Patent No.: US 9,290,452 B2
(45) Date of Patent: Mar. 22, 2016

(54) MULTICOMPONENT CRYSTALLINE SYSTEM COMPRISING DEFERASIROX AND ISONICOTINAMIDE AND A PROCESS FOR THE PREPARATION THEREOF

(71) Applicant: BASF SE, Ludwigshafen (DE)

(72) Inventors: Andreas Hafner, Gelterkinden (CH); Fritz Blatter, Reinach (CH); Eva Roedel, Basel (CH); Martin Szelagiewicz, Basel (CH); Tiziana Chiodo, Mannheim (DE); Tobias Hintermann, Therwil (CH); Beate Salvador, Ellerstadt (DE); Marcus Vossen, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/415,875

(22) PCT Filed: Aug. 5, 2013

(86) PCT No.: PCT/EP2013/066360
§ 371 (c)(1),
(2) Date: Jan. 20, 2015

(87) PCT Pub. No.: WO2014/023682
PCT Pub. Date: Feb. 13, 2014

(65) Prior Publication Data
US 2015/0175544 A1 Jun. 25, 2015

Related U.S. Application Data

(60) Provisional application No. 61/679,800, filed on Aug. 6, 2012.

(30) Foreign Application Priority Data

Aug. 6, 2012 (EP) ..................... 12179346

(51) Int. Cl.
*C07D 213/81* (2006.01)
*C07D 249/08* (2006.01)

(52) U.S. Cl.
CPC ............ *C07D 213/81* (2013.01); *C07D 249/08* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 2010/0056590 A1 | 3/2010 | Mutz | |
| 2011/0097413 A1* | 4/2011 | Neela ................... | C07D 249/08 424/489 |
| 2012/0203007 A1 | 8/2012 | Mutz | |
| 2013/0237553 A1 | 9/2013 | Hafner et al. | |
| 2014/0155371 A1 | 6/2014 | Hafner et al. | |
| 2015/0087657 A1 | 3/2015 | Hafner et al. | |

FOREIGN PATENT DOCUMENTS

| | | |
|---|---|---|
| WO | WO 2008/065123 A2 | 6/2008 |
| WO | WO 2009/130604 A2 | 10/2009 |
| WO | WO 2012/032169 A1 | 3/2012 |
| WO | WO 2012/069394 A1 | 5/2012 |
| WO | WO 2013/014604 A1 | 1/2013 |
| WO | WO 2013/084130 A1 | 6/2013 |
| WO | WO 2013/186726 A2 | 12/2013 |
| WO | WO 2013/189910 A1 | 12/2013 |
| WO | WO 2014/060449 A1 | 4/2014 |

OTHER PUBLICATIONS

U.S. Appl. No. 14/406,264, filed Dec. 8, 2014, Chiodo, et al.
U.S. Appl. No. 14/406,339, filed Dec. 8, 2014, Chiodo, et al.
U.S. Appl. No. 14/433,147, filed Apr. 2, 2015, Chiodo, et al.
European Search Report issued Oct. 22, 2012 in European Patent Application No. EP 12 17 9346.
International Search Report issued Sep. 13, 2013 in corresponding PCT/EP2013/066360 filed Aug. 5, 2013.
Nair Rodriguez-Hornedo et al: "Cocrystals: Design, Properties and Formation Mechanisms", (Oct. 2, 2006), Encyclopedia of Pharmaceutical Technology, XP008095117, pp. 615-635.
Nikoletta B. Báthori et. al: "Pharmaceutical Co-crystals with Isonicotinamide-Vitamin B3, clofibric Acid and Diclofenac -and Two Isonicotinamide Hydrates", Crystal Growth & Design, vol. 11, No. 1, 2011, pp. 75-87.
Kevin S. Eccles et al: Expending the crystal landscape of isonicotinamide: concomitant polymorphism and co-crystallisation, CrystEngComm, This journal is The Royal Society of Chemistry 2011, vol. 13, 2011, pp. 6923-6925.

* cited by examiner

*Primary Examiner* — Timothy R Rozof
(74) *Attorney, Agent, or Firm* — Oblon, McClelland, Maier & Neustadt, L.L.P

(57) ABSTRACT

The present invention refers to a multicomponent crystalline system (co-crystal) comprising a compound of formula (1) (4-[3,5-Bis(2-hydroxyphenyl)-1H-1,2,4-triazol-1-yl]benzoic acid; INN: Deferasirox) formula (1) and a compound of formula (2) (Isonicotinamide; pyridine-4-carboxamide) formula (2), as well as to a process for obtaining the same.

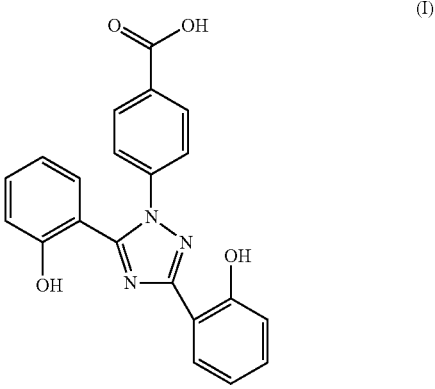

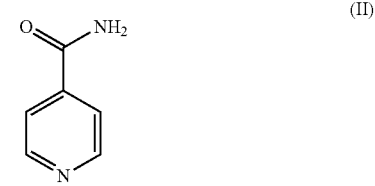

10 Claims, 2 Drawing Sheets

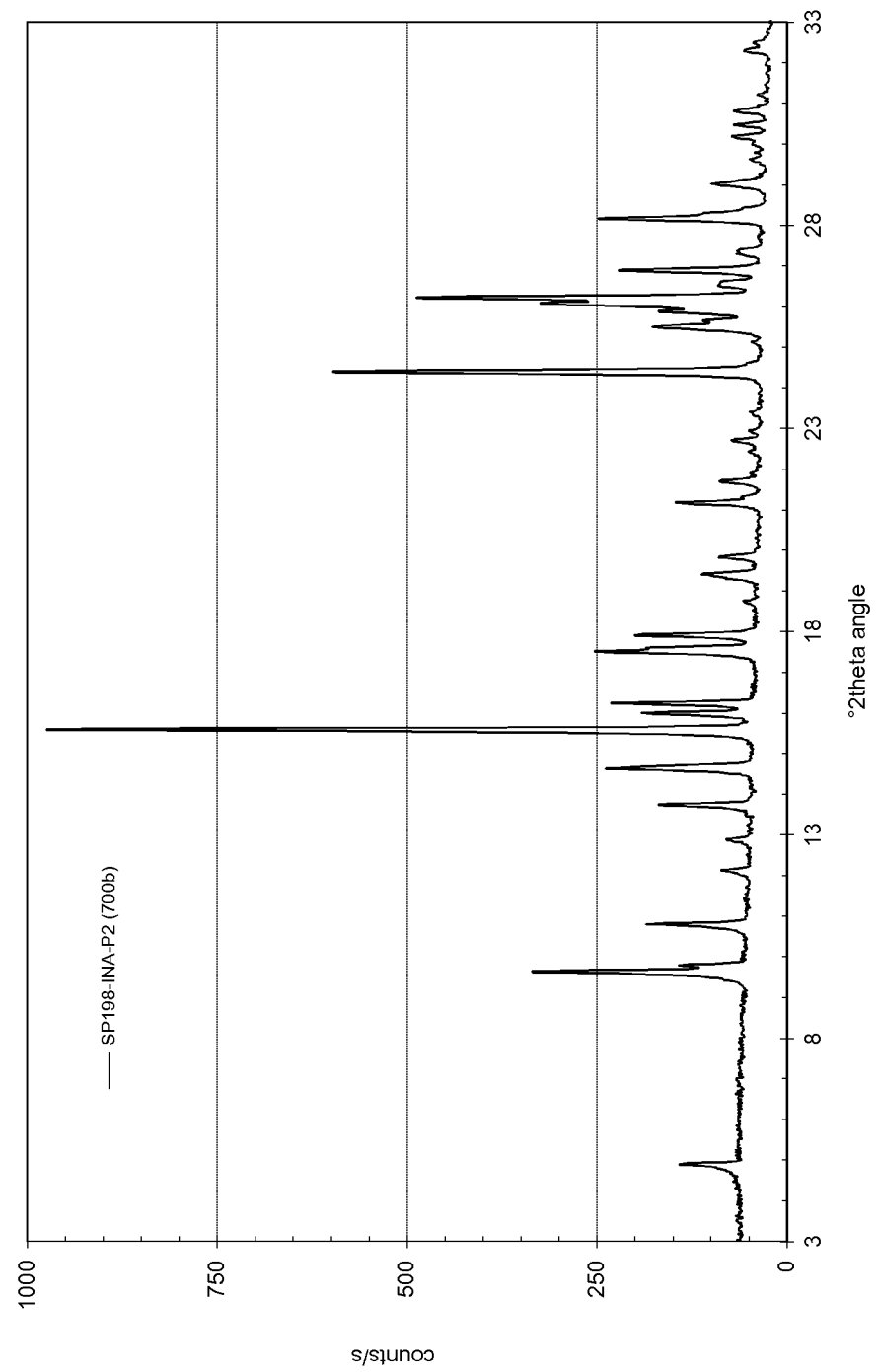
Figure 1: XRPD of Deferasirox Isonicotinamide co-crystal

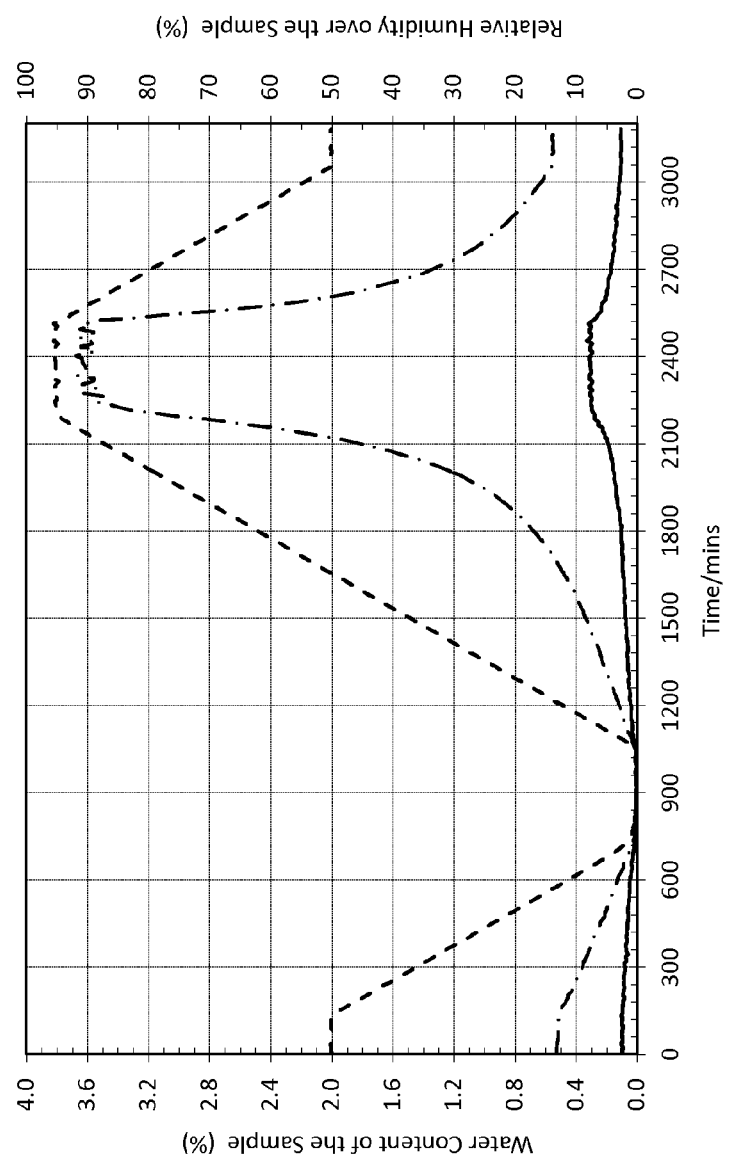

Figure 2: Dynamic Vapor Sorption behavior of the Deferasirox Isonicotinamide co-crystal and the Deferasirox Form A. The dashed line reflects the applied measurement program which involves relative humitidy change rate of 5% per hour and phases of constant humidity. The dash – dot line is the result obtained for Deferasirox Form A and the continuous line is the result for the Deferasirox Isonicotinamide co-crystal both measured under identical conditions.

MULTICOMPONENT CRYSTALLINE SYSTEM COMPRISING DEFERASIROX AND ISONICOTINAMIDE AND A PROCESS FOR THE PREPARATION THEREOF

Deferasirox (4-[3,5-bis(2-hydroxyphenyl)-1H-1,2,4-triazol-1-yl]benzoic acid) is an orally active iron chelator that is indicated in the treatment of iron overload in transfusion dependent anemias, in particular thalassemia major, thalassemia intermediate and in sickle cell disease to reduce iron-related morbidity and mortality. Deferasirox can also be used in the treatment of hemochromatosis.

The active ingredient Deferasirox is sold under the trademark EXJADE® as dispersible tablet for oral administration and comprises Deferasirox free drug substance as active ingredient.

According to the marketing authorization EXJADE® is indicated for the treatment of chronic iron overload due to frequent blood transfusions (7 ml/kg/month of packed red blood cells) in patients with beta thalassaemia major aged 6 years and older.

EXJADE® is also indicated for the treatment of chronic iron overload due to blood transfusions when deferoxamine therapy is contraindicated or inadequate in the following patient groups:

- in patients with beta thalassaemia major with iron overload due to frequent blood transfusions (≥7 ml/kg/month of packed red blood cells) aged 2 to 5 years,
- in patients with beta thalassaemia major with iron overload due to infrequent blood transfusions (<7 ml/kg/month of packed red blood cells) aged 2 years and older,
- in patients with other anaemias aged 2 years and older.

EXJADE® is dispersed by stirring in a glass of water or orange or apple juice (100 to 200 ml) until a fine suspension is obtained. After the suspension has been swallowed, any residue must be resuspended in a small volume of water or juice and swallowed.

Thus, it is important that Deferasirox as active ingredient has a very good solubility in water, which is not the case. A suspension is formed when the dispersible tablet is dispersed in water. Thus, it is possible that a patient in need of Deferasirox does not take up the entire active ingredient being present in the dispersible tablet. It might be possible that a residue remains not being administered to the patient.

WO 2008/065123 refers to several crystalline forms of Deferasirox. Several forms and in particular form A are characterized by XRPD. The solubility in water of the crystalline forms of Deferasirox disclosed is poor.

Thus, the technical problem arises to modify the prior art in order to find an administration form of Deferasirox having an improved solubility in water. However, said administration form must be stable in an environment having enhanced relative humidity like tropical countries.

The technical problem underlying the present invention is solved by a multicomponent crystalline system (co-crystal) comprising a compound of formula 1 (4-[3,5-Bis(2-hydroxyphenyl)-1H-1,2,4-triazol-1-yl]benzoic acid; INN: Deferasirox)

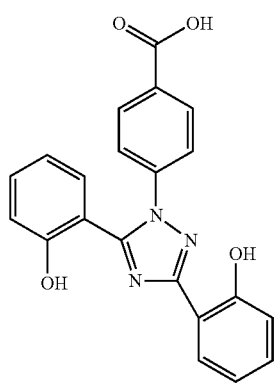

formula 1 and a compound of formula 2 (Isonicotinamide; pyridine-4-carboxamide)

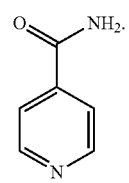

formula 2

Deferasirox is an achiral compound, since it does not bear a chiral center. Moreover, the second compound isonicotinamide is also referred to as co-crystal former.

In the context of the present invention isonicotinamide is a co-crystal former being solid at ambient temperature (in contrast to a solvate in which the second component would be liquid at ambient temperature). Thus, the multicomponent crystalline system of the present invention can be regarded as being a co-crystal.

In the context of the present invention, ambient temperature is room temperature, being preferably 20 to 30° C. and most preferably 20 to 25° C.

Preferably, the multicomponent crystalline system exhibits a molar ratio of the compound of formula 1 and the compound of formula 2 is in the range of from 1:0.75 to 1:1.25. Even more preferred, the molar ratio of the compound of formula 1 and the compound of formula 2 is in the range of from 1:0.8 to 1:1.2, preferably of from 1:0.9 to 1:1.1 and most preferred approximately 1:1.

Preferably, the multicomponent crystalline system according to the present invention has an XRPD pattern with at least one characteristic peak (expressed in 2θ±0.2° 2θ (CuKα radiation)) at 9.6, 14.6, 15.6 and/or 24.4°, preferably showing all of these peaks. Even more preferred, the multicomponent crystalline system has an XRPD pattern with at least one characteristic peak (expressed in 2θ±0.2° 2θ (CuKα radiation)) at 4.9, 9.6, 13.7, 14.6, 15.6, 24.4, 26.1 and/or 26.2°, preferably showing all of these peaks. A respective XRPD pattern is shown in FIG. 1.

However, the most important advantage of the multicomponent crystalline system of this invention is the dramatically enhanced aqueous solubility. The aqueous solubility of the Deferasirox was determined under the same conditions and according to the same protocol as the solubility of the multicomponent crystalline system (co-crystals).

The aqueous solubility of Deferasirox free drug substance and the multicomponent crystalline system of the present invention (Deferasirox-Isonicotinamide co-crystal) was determined in water at ambient temperature after about three days of suspension equilibration using HPLC for the determination of the concentration in the filtered solution. The solubility of Deferasirox free drug substance was found to be below the limit of detection which was estimated to about 1 microgram per ml, whereas the solubility of the Deferasirox-Isonicotinamide co-crystal was found to be about 32 microgram per ml.

Surprisingly, the solubility in water of the multicomponent crystalline system of the present invention is significantly higher than the solubility of Deferasirox free drug substance. The higher solubility of the multicomponent crystalline system is advantageous when formulated as disintegrating tablet.

It is known that the anhydrous form A of Deferasirox converts to a hydrate form upon exposure to high relative humidity, therefore anhydrous Deferasirox is hygroscopic. The multicomponent crystalline system described here is characterized in that it has good hygroscopic properties, i.e. absorb little water at high relative humidity. This is evident from table 1 below, which compares the water contents of the multicomponent crystalline system and Deferasirox free drug substance at 50% and 95% relative humidity. The data originate from dynamic water vapor adsorption measurements. The water vapor sorption measurement is a suitable method for investigating the hygroscopic properties of solid substances. Water vapor sorption measurements can be carried out in different ways. In general, in this connection, a small sample of ca. 10-30 mg is introduced into a microbalance in a suitable sample carrier. The sample is then exposed to different relative humidities in accordance with a defined program, the change in the sample mass being simultaneously recorded over the time. As a result, insights into the hygroscopic behavior of a substance can be obtained. Both multi-component crystalline system of the present invention and also Deferasirox free drug substance were investigated using this method and it was established that the Deferasirox free drug substance adsorbs significantly more water under identical measurement conditions and is thus more hygroscopic. It has been found that for example the multicomponent crystalline system of the present invention at 50% relative humidity contains only ca. 0.1% water, and after four hours at 95% relative humidity absorbs only just ca. 0.2% more water than at 50% relative humidity, the latter value corresponding approximately to the standard humidity conditions in central Europe. FIG. 2 illustrates that, when measured under identical conditions, the Deferasirox Isonicotinamide co-crystal shows substantially improved properties with respect to its hygroscopicity, because it is much less prone to water uptake than the Deferasirox Form A when exposed to high relative humidity conditions.

TABLE 1

Results of the water vapor sorption measurements

| | $H_2O$ content at 50% r.h. | $H_2O$ content at 95% r.h. |
|---|---|---|
| multicomponent crystalline system of the present invention | 0.1% | 0.3% |
| Deferasirox free drug substance | 0.5% | 3.6% |

This result, in particular the combination of improved solubility and better hygroscopic properties, is unexpected for the person skilled in the art and cannot be deduced from the prior art. Consequently, the multicomponent crystalline system of the present invention offers a profile of properties which is advantageous for use in medicaments and preferably in disintegrating tablets.

A further aspect of the present invention is the multicomponent crystalline system and the respective pharmaceutical composition for use in the treatment of iron overload in transfusion dependent anemias, in particular thalassemia major, thalassemia intermediate and/or in sickle cell disease to reduce iron-related morbidity and mortality and/or in the treatment of hemochromatosis.

Preferably, the multicomponent crystalline system and the respective pharmaceutical composition can be used for the treatment of chronic iron overload due to frequent blood transfusions in patients with beta thalassaemia being preferably major aged 6 years and older.

The multicomponent crystalline system of the present invention and the respective pharmaceutical composition can also be used for the treatment of chronic iron overload due to blood transfusions when deferoxamine therapy is contraindicated or inadequate, preferably in the following patient groups:

in patients with beta thalassaemia major with iron overload due to frequent blood transfusions (≥7 ml/kg/month of packed red blood cells) aged 2 to 5 years, in patients with beta thalassaemia major with iron overload due to infrequent blood transfusions (<7 ml/kg/month of packed red blood cells) aged 2 years and older, in patients with other anaemias aged 2 years and older.

Another object of the present invention is a process for obtaining the multicomponent crystalline system of the present invention comprising the steps of:

a) providing a compound of formula 1 (INN: Deferasirox)

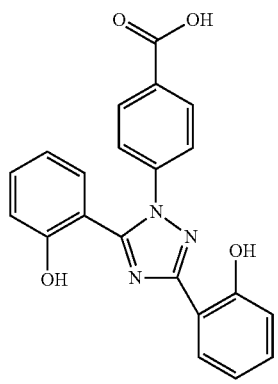

formula 1 in a suitable solvent or a mixture of solvents;

b) adding a compound of formula 2 (Isonicotinamide)

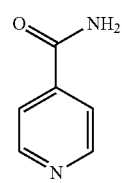

formula 2 to the mixture of step a);

c) optionally concentrating the composition of step b);

d) crystallizing;

e) optionally equilibrating the obtained suspension of step d); and f) isolating the obtained precipitate.

Preferably, the molar ratio of the compound of formula 1 in step a) and the compound of formula 2 in step b) is in the range from 1:0.75 to 1:5.

Preferably, in step b) the compound of formula 1 is provided in solid form, or as a solution in an ether, an alcohol, a ketone, an acetate, of mixture of solvents optionally containing water.

Preferably, the solvent used in step a) is an organic solvent such as an alcohol, ether or ketone (e.g. tetrahydrofuran, acetone, methanol, ethanol, propanol, butanol). Preferably, the solvent is a mixture of tetrahydrofuran, ethanol, methanol and/or acetone.

Solutions or suspension according to steps a) and/or b) preferably are concentrated solutions. Preferably, the solvent is an organic solvent such as an alcohol, ether or ketone (e.g. tetrahydrofuran, acetone, methanol, ethanol, propanol, butanol the solvent is a mixture of tetrahydrofuran, ethanol, methanol and/or acetone.

In a further preferred embodiment, in step d) and/or e) seed crystals are added.

The herein described multicomponent crystalline system shows good kinetic and thermodynamic stability.

The multicomponent crystalline system is generally obtained as a fine powder with typical particle size distributions with the median size between 1 and 50 µm, preferably between 1 to 10 µm. This particle size range ensures a fast dissolution profile, while retaining the favorable handling properties in the formulation process.

However, the most important advantage of the multicomponent crystalline system of the present invention is the dramatically enhanced aqueous solubility.

A further aspect of the present invention is a pharmaceutical composition comprising the multicomponent crystalline system of the present invention and optionally one or more pharmaceutically acceptable excipients.

Oral formulations may be solid formulations such as capsules, tablets, pills and troches, or a liquid suspension formulation.

The crystalline composition according to the invention may be used directly as powders (micronized particles), granules, suspensions, or they may be combined together with other pharmaceutically acceptable ingredients in admixing the components and optionally finely divide them, and then filling capsules, composed for example from hard or soft gelatin, compressing tablets, pills or troches, or suspend in suspensions. Coatings may be applied after compression to form pills.

Pharmaceutically acceptable ingredients are well known for the various types of formulation and may be for example binders such as natural or synthetic polymers, excipients, disintegrants, lubricants, surfactants, sweetening and other flavouring agents, coating materials, preservatives, dyes, thickeners, adjuvants, antimicrobial agents and carriers for the various formulation types.

Examples for binders are gum tragacanth, acacia, starch, gelatin, and biological degradable polymers such as homo- or co-polyesters of dicarboxylic acids, alkylene glycols, poly-alkylene glycols and/or aliphatic hydroxyl carboxylic acids; homo- or co-polyamides of dicarboxylic acids, alkylene diamines, and/or aliphatic amino carboxylic acids; corresponding polyester-polyamide-co-polymers, polyanhydrides, polyorthoesters, polyphosphazene and polycarbonates. The biological degradable polymers may be linear, branched or crosslinked. Specific examples are poly-glycolic acid, poly-lactic acid, and poly-d,l-lactide/glycolide. Other examples for polymers are water-soluble polymers such as polyoxaalkylenes (polyoxaethylene, polyoxapropylene and mixed polymers thereof, poly-acrylamides and hydroxylalkylated polyacrylamides, poly-maleic acid and esters or -amides thereof, poly-acrylic acid and esters or -amides thereof, poly-vinylalcohol und esters or -ethers thereof, poly-vinylimidazole, poly-vinylpyrrolidon, und natural polymers like chitosan, carragenan or hyaluronic acid.

Examples for excipients are phosphates such as dicalcium phosphate.

Examples for disintegrants are croscarmellose sodium, crospovidone, low-substituted hydroxypropyl cellulose, sodium starch glycolate or alginic acid.

Surfactants may be anionic, cationic, amphoteric or neutral. Examples for surfactants are lecithin, phospholipids, octyl sulfate, decyl sulfate, dodecyl sulfate, tetradecyl sulfate, hexadecyl sulfate and octadecyl sulfate, Na oleate or Na caprate, 1-acylaminoethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2- sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctylsulfosuccinate, cocamidopropylbetaine and laurylbetaine, fatty alcohols, cholesterols, glycerol mono- or -distearate, glycerol mono- or -dioleate and glycerol mono- or -dipalmitate, and polyoxyethylene stearate.

Examples for sweetening agents are sucrose, fructose, lactose or aspartam.

Examples for flavouring agents are peppermint, oil of wintergreen or fruit flavours like cherry or orange flavour.

Examples for coating materials are gelatin, wax, shellac, sugar or biological degradable polymers.

Examples for preservatives are methyl or propylparabens, sorbic acid, chlorobutanol, phenol and thimerosal.

Examples for adjuvants are fragrances.

Examples for thickeners are synthetic polymers, fatty acids and fatty acid salts and esters and fatty alcohols.

Examples for solid carriers are talc, clay, microcrystalline cellulose, silica, alumina and the like.

The formulation according to the invention may also contain isotonic agents, such as sugars, buffers or sodium chloride.

Preferably, the pharmaceutical composition comprising the multicomponent crystalline system is a dispersible tablet. The multicomponent crystalline system of the present invention may also be formulated as effervescent tablet or powder, which can disintegrate in an aqueous environment to provide a drinking solution.

The most preferred route is oral administration. The dosages may be conveniently presented in a unit dosage form and prepared by any of the methods well-known in the art of pharmacy Capsule dosages, of course, will contain the solid composition within a capsule which may be made of gelatin or other conventional encapsulating material. Tablets and powders may be coated. Tablets and powders may be coated with an enteric coating. The enteric coated powder forms may have coatings comprising phthalic acid cellulose acetate, hydroxypropylmethyl-cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

The multicomponent crystalline system of the present invention and its formulations, respectively, can be also being administered in combination with other therapeutic agents being effective to treat a given condition and/or to provide a combination therapy.

BRIEF DESCRIPTIONS OF THE DRAWINGS

FIG. 1 shows an XRPD pattern of Deferasirox Isonicotinamide co-crystal.

FIG. 2 shows a Dynamic Vapor Sorption behavior of the Deferasirox Isonicotinamide co-crystal and the Deferasirox Form A.

Abbreviations

HPLC high pressure liquid chromatography
NMR nuclear magnetic resonance
TGA thermogravimetric analysis
r.h. relative humidity (air, if not indicated otherwise)
v/v volume by volume
XRPD X-ray powder diffraction
DVS dynamic vapor sorption Instrumental X-Ray Powder Diffraction The measurements were carried out with a Stoe Stadi P with a Mythen1 K Detector and Cu-Kα1 radiation. Measurement conditions: transmission; 40 kV and 40 mA tube power; curved Ge monochromator; 0.02° 2θ step size, 12 s step time, 1.5-50.5° in 2θ scanning range; detector mode: step scan; 1° 2θ detector step; standard sample preparation: 10 to 20 mg sample was placed between two acetate foils; sample holder: Stoe transmission sample holder; the sample was rotated during the measurement.

Generally, the 2θ values are accurate within an error of ±0.1-0.2°. The relative peak intensities can vary considerably for different samples of the same crystalline form because of different preferred orientations of the crystals.

Thermogravimetric Analysis (TGA)

TGA was performed with a TA Instruments TGA Q5000 instrument at a heating rate of 10° per minute from 25 to 300° C.

1H-NMR

The 1H-NMR spectra were recorded on a Bruker DPX 300 spectrometer. Solvent: D6-DMSO Solubility Determinations Solubility determinations were carried out in pure water at 25±2° C. Suspensions with about 50 mg the solid form, either the co-crystal of the present invention or deferasirox free drug substance in 7 mL water were prepared an equilibrated for three days before the solution phase was filtered off and tested by HPLC.

HPLC

HPLC was carried out on an Agilent 1100 HPLC chromatograph equipped with a UV-vis detection unit. The column type used was a Waters XTerra MS C18, 100×4.6 mm, 5 µm (FK-CC01F). The applied gradient method with eluent A (water containing 1% of trifluoroacetic acid) and eluent B (acetonitrile) was as follows: At t=0 minutes: 95% A, 5% B, 20 minutes: 5% A, 95% B, 20.5 minutes: 95% A and 5% B, 25 minutes: 95% A, 5% B. The applied flow rate was 1.0 mL per minute, the injection volume was 10 microliter and the detection wavelength was 254 nm.

Water Vapor Adsorption Measurements (DVS)

Dynamic water vapor adsorption measurements were carried out using an SPS11 100 n instrument, manufactured by "Projekt Messtechnik" in Ulm, Germany. For this, ca. 20 mg of the sample were weighed into an aluminum support and this was inserted into the measurement chamber of the instrument. The sample was then subjected to preselected relative humidities in accordance with a defined program, the change in mass being determined over the time. The following measurement program was used: 50% r.h. constant for two hours, then changing the relative humidity to 0% r.h., then changing the relative humidity to 96% r.h., constant at 96% r.h. for four hours and then changing the relative humidity to 50% r.h. and then constant at 50% r.h. for one hour. The change rates set were in each case 5% per hour.

Solvents: For all experiments, Fluka or Sigma Aldrich grade solvents are used. Selected solvents are dried using 3 or 4 Å molecular sieves.

The following examples illustrate the invention.

EXAMPLE 1

To 51 mg isonicotinamide and 150 mg Deferasirox was added 100 µl methanol. This mixture was vigorously ground to dryness in an agate mortar. Then another 100 µl methanol was added and grinding was carried out. Investigation of the solid material by XRPD shows that an new solid form that is still containing some Deferasirox form A is obtained. The mixture of the multicomponent crystalline system with Deferasirox form A was further processed by addition of 4 ml of acetone. The resulting suspension was shortly heated to reflux temperature and then stirred at r.t in an open vial allowing about 3 ml of the solvent to evaporate before the solid was separated by filtration. Investigation of the resulting crystalline material by XRPD shows a powder pattern as shown in FIG. 1 with peak locations as provided in table 2. Further analysis by H-NMR reveals a molar ratio of about 1:1 of Deferasirox and Isonicotinamide.

EXAMPLE 2

882 mg of Deferasirox and 290 mg of isonicotinamide are dissolved in a mixture of 15 ml acetone and 3 ml THF by shortly heating to reflux temperature. Let the solution cool to room temperature and evaporate the solvents under a flow of nitrogen with a flow rate about 50 ml per minute. To the dry residue 5 ml acetone is added and the resulting suspension is stirred at room temperature for two hours before the solid is filtered off. The obtained crystalline material is investigated by XRPD, TGA, H-NMR and dynamic vapor sorption analysis. H-NMR spectros-copy of the solid material indicates a molar ratio of Deferasirox to Isonicotinamide of about 1:1. Thermogravimetric analysis shows no significant mass loss below 150° C. and therefore we conclude that the co-crystal is neither a solvate nor a hydrate. Powder X-ray diffraction shows a XRPD pattern that is characteristic for the Deferasirox-Isonicotinamide co-crystal as depicted FIG. 1 and with peak locations as set out in table 2. The aqueous solubility at room temperature is tested by equilibrating a suspension of about 50 mg of the solid product in 7 ml purified water over three days. Then suspension is filtered and the concentration in the solution determined by HPLC. The solubility in water at 25±2° C. is about 32 microgram per mL. The dynamic water vapor sorption diagram is exemplified in FIG. 2 and the water content at 50% and 95% relative humidity is given in table 1.

TABLE 2

XRPD peak locations for the Deferasirox Isonictinamide co-crystal

| 2θ angle | d-spacing Å | Qualitative intensity |
|---|---|---|
| 4.9 | 18.2 | w |
| 9.6 | 9.2 | s |
| 10.8 | 8.2 | w |
| 12.1 | 7.3 | vw |
| 12.8 | 6.9 | vw |
| 13.7 | 6.4 | w |
| 14.6 | 6.0 | m |
| 15.6 | 5.69 | vs |
| 16.0 | 5.53 | m |
| 16.2 | 5.45 | m |
| 17.5 | 5.05 | m |
| 17.9 | 4.95 | m |
| 19.4 | 4.58 | w |
| 19.8 | 4.47 | w |
| 21.2 | 4.19 | w |
| 21.7 | 4.09 | w |
| 22.7 | 3.91 | w |
| 24.4 | 3.65 | s |
| 25.5 | 3.49 | m |
| 25.9 | 3.44 | m |
| 26.1 | 3.41 | s |
| 26.2 | 3.40 | s |
| 26.6 | 3.35 | vw |
| 26.9 | 3.31 | m |
| 28.2 | 3.16 | m |
| 29.0 | 3.07 | w |
| 30.8 | 2.90 | w |
| 32.3 | 2.77 | w |
| 33.9 | 2.64 | vw |
| 35.4 | 2.53 | w |
| 38.1 | 2.36 | vw | vs = very strong,
s = strong,
m = medium,
w = weak,
vw = very weak

The invention claimed is:

1. A multicomponent crystalline system, comprising a compound of formula 1, which is 4-[3,5-Bis(2-hydroxyphenyl)-1H-1,2,4-triazol-1-yl]benzoic acid:

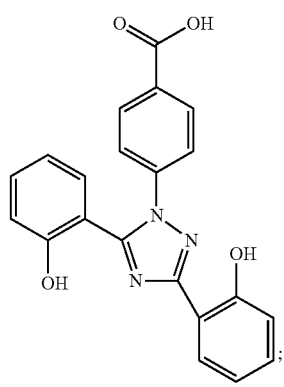

formula 1 and a compound of formula 2, which is isonicotinamide; pyridine-4-carboxamide:

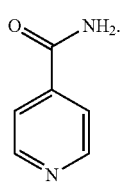

formula 2

2. The multicomponent crystalline system according to claim 1, wherein a molar ratio of the compound of formula 1 to the compound of formula 2 is from 1:0.75 to 1:1.25.

3. The multicomponent crystalline system according to claim 1, wherein the system has an XRPD pattern with a characteristic peak, expressed in 2θ±0.2° 2θ (CuKα radiation) at 9.6, 14.6, 15.6 and/or 24.4°.

4. The multicomponent crystalline system according to claim 3, wherein the system has an XRPD pattern with a characteristic peak, expressed in 2θ±0.2° 2θ (CuKα radiation) at 4.9, 9.6, 13.7, 14.6, 15.6, 24.4, 26.1 and/or 26.2°.

5. The multicomponent crystalline system according to claim 1, wherein the system is suitable for treatment of iron overload in transfusion dependent anemias to reduce iron-related morbidity and mortality, for the treatment of hemochromatosis, or both.

6. A process for obtaining the crystalline composition according to claim 1, comprising:
a) adding a compound of formula 1

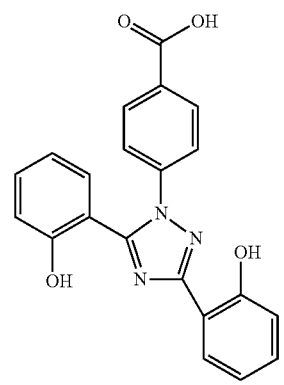

formula 1 in a solvent or a mixture of solvents to obtain a mixture;

b) adding a compound of formula 2

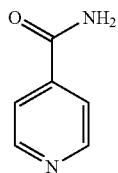
formula 2 to the mixture obtained in the adding a) to form a composition;

c) optionally concentrating the composition obtained in the adding b);

d) crystallizing to obtain a suspension;

e) optionally equilibrating the obtained suspension of the crystallizing d) to obtain a precipitate; and f) isolating the obtained precipitate.

7. The process according to claim 6, wherein a molar ratio of the compound of formula 1 in the adding a) to the compound of formula 2 in the adding b) is from 1:0.75 to 1:5.

8. The process according to claim 6, wherein in the adding b), the compound of formula 1 is in solid form, or as a solution in an ether, an alcohol, a ketone, an acetate, or a mixture of solvents optionally comprising water.

9. The process according to claim 6, wherein in the crystallizing d) and/or the equilibrating, e) seed crystals are added.

10. A pharmaceutical composition comprising the multi-component crystalline system according to claim 1 and optionally a pharmaceutically acceptable excipient.

* * * * *